United States Patent [19]

Sustmann

[11] Patent Number: 4,661,101
[45] Date of Patent: Apr. 28, 1987

[54] LAYERED CATAMENIAL DEVICE

[75] Inventor: Scarlet Sustmann, Viersen, Fed. Rep. of Germany

[73] Assignee: Vereinigte Papierwerke, Schickedanz & Co., Nuremberg, Fed. Rep. of Germany

[21] Appl. No.: 734,376

[22] Filed: May 15, 1985

[30] Foreign Application Priority Data

May 18, 1984 [DE] Fed. Rep. of Germany ....... 3418521

[51] Int. Cl.$^4$ .............................................. A61F 13/16
[52] U.S. Cl. .................................... 604/360; 604/374; 604/375; 604/904
[58] Field of Search ............... 604/286, 285, 904, 358, 604/365, 367, 369, 374, 375, 376, 377, 378, 359, 360

[56] References Cited

U.S. PATENT DOCUMENTS

| 2,856,330 | 10/1958 | Vagenius | 167/84 |
| 3,100,035 | 8/1963 | Murphy | 194/48 |
| 3,340,874 | 9/1967 | Burgeni | 604/904 X |
| 3,618,605 | 10/1971 | Glassmann . | |
| 3,693,622 | 9/1972 | Jones, Sr. . | |
| 3,999,549 | 12/1976 | Poncy et al. . | |
| 4,020,841 | 5/1977 | Poncy et al. . | |
| 4,077,409 | 3/1978 | Murray et al. . | |
| 4,308,867 | 1/1982 | Roseman et al. | 604/904 X |
| 4,340,055 | 7/1982 | Sneider . | |
| 4,405,323 | 9/1983 | Auerbach | 604/285 |

FOREIGN PATENT DOCUMENTS

| 3135410 | 7/1969 | Fed. Rep. of Germany . |
| 1491170 | 7/1969 | Fed. Rep. of Germany . |
| 1499358 | 9/1966 | France . |
| 1504077 | 11/1966 | France . |
| 1499788 | 11/1967 | France . |
| 2083748 | 3/1982 | United Kingdom . |

OTHER PUBLICATIONS

Chemical Abstracts; 69: 78373t (1968).
Modified Cellulosies, T. L. Vigo, Antibacterial Fibers, Academic Press, pp. 260-284, New York, 1978.

Primary Examiner—John D. Yasko
Attorney, Agent, or Firm—Ernest G. Szoke; Henry E. Millson, Jr.; Mark A. Greenfield

[57] ABSTRACT

This invention affords catamenial devices such as tampons and panty liners in which a microbistatic fibrous material is layered or covered with a non-microbistatic fibrous material.

32 Claims, 8 Drawing Figures

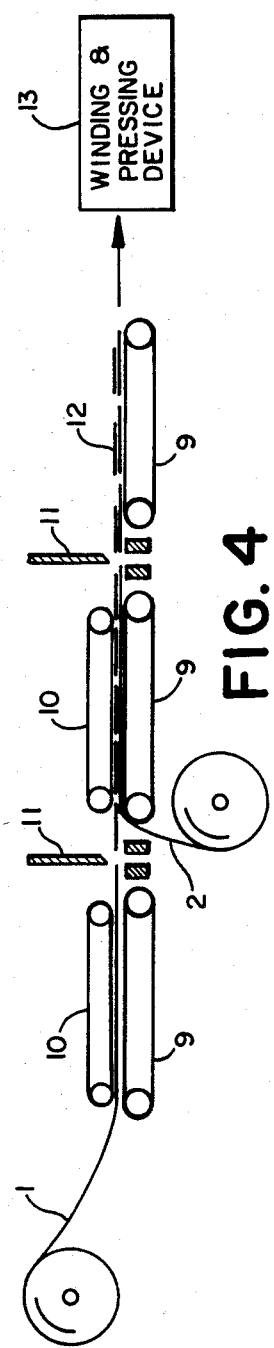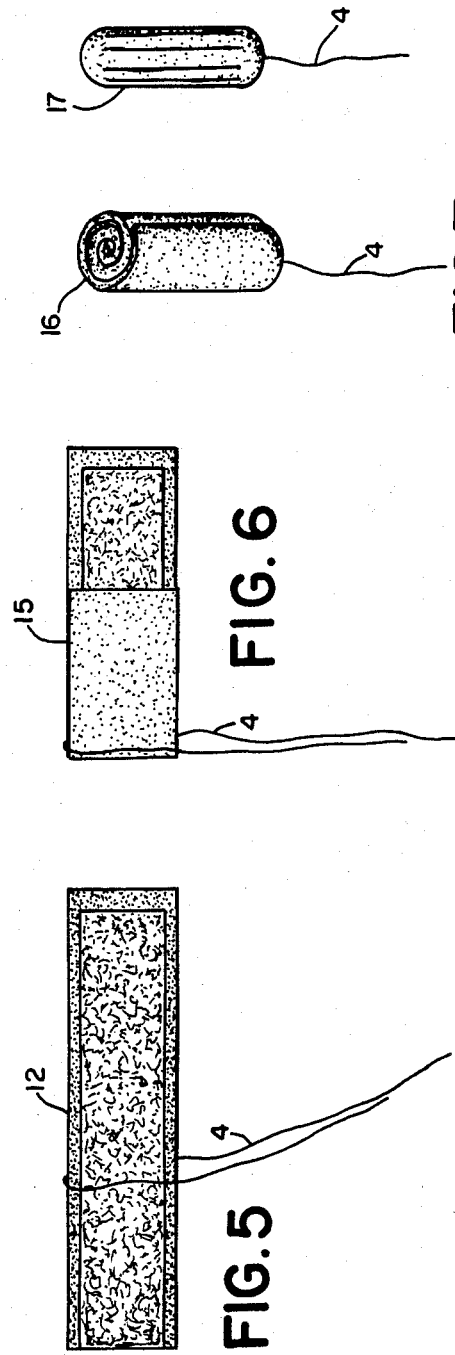

LAYERED CATAMENIAL DEVICE

BACKGROUND OF THE INVENTION

1. Field of the Invention

This invention relates to a catamenial device comprising an outer layer of fibrous cellulose untreated or treated material and an inner layer partially or completely comprising an absorbent, microbistatic fibrous material.

2. Statement of the Related Art

Catamenial tampons, and the like, comprising an absorbent fibrous material and which are used to absorb bodily secretions such as menstrual fluid, blood, and urine are well known. It is also well known that these secretions decompose after only a short time under the effect of ubiquitous microbes, accompanied by the emission of an undesirable odor. Furthermore, the growth of pathogenic microbes may present serious health risks. There have been many attempts to provide sanitary hygiene aids of absorbent fibrous materials with a deodorizing and/or microbistatic finish. Various microbicides and deodorants suitable for suppressing body odor have been proposed for this purpose.

It has also been proposed to use copper compounds for finishing fibrous material used for sanitary hygiene aids.

U.S. Pat. No. 4,385,632 (and corresponding German application No. 31 35 410) describe a catamenial absorbent pad of cellulose fibers or cotton wool which is sprayed with a solution of a copper salt or is produced from fibers or cotton wool treated with such a solution. The salts are copper borate, sulfate, chloride, formate, oxalate, tartrate, citrate, lactate, and especially, acetate.

*Chemical Abstracts*, 69:78373t (1968), relating to an article in Russian by Snezhko, et al., discloses the partial carboxymethylation of a cotton fabric followed by immersion in aqueous $AgNO_3$ or $Cu(OAc)_2$ solution, which resulted in fabrics containing chemically bound Ag or Cu. Such fabrics are disclosed as not supporting the growth of *B. subtilis* 633, *B. cereus* var *mycoides*, or *S. aureus* 209, even after 30 launderings. The immersion of the fabric in $AgNO_3$ or $Cu(OAc)_2$ without prior carboxymethylation failed to impart any lasting bacteristatic properties to the fabric.

Published European patent application No. 19,371 describes a blood-coagulating absorbent material which consists of a water-swellable, covalently crosslinked anionic polyelectrolyte, for example crosslinked carboxymethyl cellulose, which is treated with transition metal ions, such as with copper ions. Disclosed salts for treatment include copper chlorides, nitrates, sulphates, and acetates in one process, and copper carbonates, oxides or hydroxides in a second process. However, materials such as these are not usually fibrous or cannot readily be converted into fibers, wadding or nonwovens. It is disclosed that the materials may be processed with a fibrous carrier as a support when used in hygiene aids. Both the manufacture and also the processing of this material are difficult.

Microbistatically modified cellulose fibers, at least some of which may be utilizable in catamenial tampons, are described in *Modified Cellulosics* by T. L. Vigo in the chapter "Antibacterial Fibers", Academic Press, New York (1978) at pages 260–284.

Laminated catamenial tampons are disclosed in various patents. U.S. Pat. No. 4,020,841 discloses a catamenial tampon which has an absorbent core and a closed cell foam sheath closed at its outer end. U.S. Pat. No. 3,618,605 discloses a laminated catamenial tampon with a central absorbent core which is a cup-shaped. U.S. Pat. No. 3,100,035 discloses a catamenial tampon with an outer absorbent cover over an expanding core. U.S. Pat. No. 3,999,549 discloses a catamenial tampon with a resilient outer sheath surrounding an absorbent, relatively rigid, fibrous core. None of the foregoing patents appreras to disclose a chemically treated core or outer layer.

German published patent application No. 14 91 170 (Derwent No. 72911) whose inventor is A. A. Burgeni, and for which an unidentified U.S. patent is believed to have issued, discloses a catamenial tampon having a core of fine count fibers surrounded by fiber layers of increasingly coarser count, with an annular sheath of cellulose fibers surrounding the whole.

U.S. Pat. No. 4,077,409 discloses an encapsulated catamenial tampon whose core is resiliently compressed polyurethane which may have the physical addition of a deodorant, disinfectant, medicament, etc., and whose outer layer is a perforated gelatin capsule.

U.S. Pat. No. 4,340,055 discloses a catamenial tampon having an absorbent core, nonwoven outer layer, and a medication in powdered or crystalline form between the two. In another embodiment, the outer layer itself xay be impregnated.

U.S. Pat. No. 3,693,622 discloses a catamenial tampon comprising coplanar multiple plies of thin absorbent tissue paper in which the end opposite the insertion end is impregnated with non-toxic, waste fluid repellant compositions.

The use of microbicidal and deodorizing finishes in catamenial tampons has been attended above all by the disadvantage that direct contact of the microbicide or of the microbicidally finished fibrous material with the sensitive vaginal mucosa can give rise to undesirable inflammation and, above all, to harmful disturbance of the natural vaginal bacterial flora with all the unhealthiness which that causes.

SUMMARY OF THE INVENTION

The foregoing disadvantages are largely avoided by this invention's catamenial tampon, and the like, which comprises a microbistatic or microbicidal and deodorizing fibrous absorbent core (or inner layer) and an outer covering of an untreated, pH-regulating, or buffered fibrous, cellulose material.

The outer covering prevents the microbistatic core of the tampon from coming into direct contact with the body, and thus avoids the specific disadvantages of known treated materials. The outer covering may be an untreated material, or may be treated with a physiologically compatible pH-regulating or buffering agent.

The compound catamenial tampon of this invention permits menstrual and other body fluids to pass through the non-irritative outer layer, after which they are absorbed in the microbistatic and deodorizing core. As a result, undesirable microbial growth is prevented or at least held to a minimum, and the toxins, odors, irritating agents, and the like, which are the by-products of these undesirable microbes, are not produced. Since a major objective of this invention is to prevent the microbistatic agent from contacting the sensitive vaginal mucosa, it is critical that the microbistatic agent be firmly anchored to the core, so that it cannot leach through the outer layer.

The preferred microbistatic agent according to this invention is afforded by using for the core of the tampon a fibrous cellulose material modified by anionic moieties and finished with microbistatically active cations attached to those moieties. In the context of this invention, fibrous cellulosic material is understood to be cellulose, cotton and/or viscose fibers.

The preferred microbistatic (and microbicidal and/or deodorizing) fibrous core material has already been described (in respect of cupric cations) in U.S. patent application Ser. No. 06/707,706 and corresponding German patent application Ser. No. P 34 08 130, as well as in U.S. patent application Ser. No. 06/708,139 and corresponding German patent application No. P 34 08 131, all of which are incorporated herein by reference.

Other than in the operating examples, or where otherwise indicated, all numbers expressing quantities of ingredients, reaction conditions, or defining ingredient parameters used herein are to be understood as modified in all instances by the term "about".

Anionic salt-forming moieties may be incorporated in the cellulose molecule in various ways. Anionically modified cellulose fibers such as these are known and, in some cases, are also commercially available. Suitable cellulose fibers of the type in question are, for example, cellulose fibers which carry at least one of the moieties of the general formulae: $-PO_3H^{(-)}$; $-(CH_2)_n-PO_3H^{(-)}$; $-(CH_2)_n-SO_3^{(-)}$; or $(CH_2)_n-COO^{(-)}$; (where n may have a value of from 1 to 3); which are attached via the oxygen to the anhydroglucose units. Known cellulose derivatives of this type include: cellulose phosphate obtainable by esterifying cellulose with phosphoric acid: phosphonoethyl cellulose obtainable by etherifying alkali cellulose with chloroethyl phosphonate: phosphonomethyl cellulose obtainable by etherifying cellulose with chloromethyl phosphonate: sulfoethyl cellulose obtainable by etherifying cellulose with chloroethane sulfonate and the similarly obtainable sulfomethyl cellulose and sulfopropyl cellulose. Also useful is 1-sulfo-2-hydroxypropyl cellulose which may be obtained by cellulose etherification with 1-chloro-2-hydroxypropane sulfonate.

Carboxyl groups may be introduced into the cellulose molecule in two basically different ways:

by the physical incorporation of carboxyl-containing compounds in the viscose, i.e. in a cellulose dissolved in the form of cellulose xanthogenate, to form incorporated viscose fibers (alloy fibers) or by the chemical reaction (etherification) of the fiber-forming cellulose with carboxyl-containing reagents to form cellulose fibers uniformly modified by, for example, carboxyalkyl groups corresponding to the formula $-(CH_2)_n-COOH$, in which n may have a value of from 1 to 3.

The physical incorporation of compounds containing carboxyl groups in the viscose is obtained, for example, by the addition of alkali salts of acrylic acid homopolymers, acrylic acid-methacrylic acid copolymers, methyl vinyl ether-maleic acid anhydride copolymers, alginic acid or carboxymethyl cellulose to the viscose solution, followed by spinning in the usual way into a precipitation bath. Commercially available fibers of the type include fibers which are a blend of viscose and acrylic acid-methylacrylic acid copolymer, sold by Enka under the trademark ABSORBIT. Fibers such as these are not uniformly modified, but instead are made up of modified and unsubstituted fiber fragments.

Cellulose fibers chemically modified throughout by carboxyalkyl groups are particularly preferred for producing the fibrous core materials of this invention. In fibers such as these, the entire fiber-forming cellulose is uniformly modified. They may be obtained by carboxymethylating cellulose fibers with sodium chloroacetate, immediately after conversion into alkali cellulose. The cellulose thus modified may be improved in its fiber structure by the viscose spinning process. However, a viscose fiber regenerated by the viscose spinning process may also be subsequently carboxymethylated with chloroacetic acid. A third possibility of obtaining cellulose fibers uniformly modified with carboxyalkyl groups is to add sodium chloroacetate to the viscose solution during xanthogenation and then spin the carboxymethylated viscose in the usual way. Viscose fibers such as these, uniformly modified by carboxymethyl groups, are commercially available from Lenzing AG under the trademark VISCOSORB IN.

If acrylonitrile is added to the viscose solution during xanthogenation, viscose fibers consisting of carboxyethyl cellulose having a low degree of substitution are obtained on completion of the viscose spinning process. Fibers such as these are commercially available from FMC Corporation under the trademark BAR (Bondable Avisco Rayon) fibers.

Other reagents suitable for uniformly modifying the viscose by addition to the viscose solution during xanthogenation are sodium vinyl sulfonate, sodium chloromethane sulfonate, and sodium chloromethane phosphonate. Uniformly chemically modified viscose fibers containing sulfoethyl groups, sulfomethyl groups and phosphonomethyl groups are obtained in this way.

However, a fibrous cellulose chemically modified throughout by carboxyl groups and, more especially, by carboxymethyl groups is particularly preferred for producing the cores of the catamenial tampons according to this invention. A fibrous material obtained from a carboxy-methyl-modified cellulose regenerated by the viscose spinning process is especially suitable.

Microbistatically active cations suitable for finishing the fibrous cellulose material modified by anionic moieties are heavy metal ions and ions of transition metals, such as copper, silver, zinc, cadmium, chromium and nickel, and also quaternary ammonium ions such as the cetyl trimethyl-ammonium ion or the lauryl dimethyl benzylammonium ion or any mixture thereof. Cupric ($Cu^{+2}$) ions are particularly preferred for finishing the cellulose materials modified with anionic moieties.

The cellulose derivatives suitable for producing the fibrous core material to be used in accordance with this invention should have such a high degree of substitution, based on the anionic salt-forming groups, that they are capable of binding from 0.1 to 3.0% by weight of copper, based on the weight of the fibrous material. The most suitable carboxymethyl-modified viscose fibers for the fibrous material according to the invention have a degree of substitution of from 0.01 to 0.3, i.e.; they contain on average from about 0.01 to 0.3 carboxymethyl groups per anhydroglucose unit. When the cation is copper, it should make up from 0.1 to 2.0% by weight and preferably from 0.2 to 0.8% by weight of the fibrous material.

It has also proved to be of advantage for the fibrous core material used in accordance with the invention to have a fiber pH-value, as measured in accordance with German Industrial Norm (DIN) 54,275, of from 4 to 5. The effect of a fiber pH of this order is that the fibrous materials according to the invention have an additional buffer effect on absorbed body liquids and thus help in establishing a physiologically favorable, mildly acidic pH on the skin surface, so that inflammation and susceptibility to alkaliphilic microbial disorders are avoided.

The fibrous core material to be used for the catamenial tampons according to the invention should have—in another preferred embodiment—a high water retention capacity of at least 80%, as measured in accordance with German Industrial Norm (DIN) 53,814.

The fibrous core material used in accordance with the invention may readily be produced from known fibers containing anionic salt-forming moieties by treating the fibers containing anionic salt-forming moieties with an aqueous salt solution, for example a chloride or sulfate of the microbistatically active cations, and washing the fibers with water until they are substantially free from salt, followed by drying.

The high water retention fibrous material preferably employed may readily be produced by using a carboxymethyl viscose fiber having a degree of substitution of from 0.01 to 0.3 and a correspondingly high water retention capacity. For example, the commercially available VISCOSORB 1S fibers (a trademark of Lenzing AG) having a water retention capacity of approximately 200% and a degree of substitution of about 0.1, may be used either in the sodium salt form or after conversion into the free acid form.

In producing the core fibers used in this invention, any salt of the foregoing cations may be used, provided that it is water soluble, has an anion which can be displaced in an ion-exchange reaction with the anionic salt-forming moieties of the modified cellulose fibers, and is physiologically compatible. The anionic salt-forming moieties of the modified cellulose fibers are preferably capped with hydrogen cations, although other cations may be employed, depending upon the salt used and the presence of an acid. The use of a physiologically compatible salt is only important because residual traces of the salt may remain in the cellulose fiber after treatment. The preferred cation is $Cu^{+2}$(cupric). Useful cupric salts are the chloride, nitrate, sulfate, or acetate, or the carbonate, oxide, or hydroxide, depending upon the treatment method, with cupric sulfate being preferred. A solution of from 1 to 20 g/l of cupric sulfate ($CuSO_4 . 5 H_2O$) in water is one example of a particularly suitable aqueous cupric salt solution.

Once the cation is attached to the anionic moiety of the cellulose fiber, the manner of production is irrelevant to the finished fiber.

The treatment is generally carried out in the absence of heat for a period of 1 to 60 minutes, 20 to 40 minutes being preferred. Thereafter, the salt solution is removed from the fiber, for example by pressing, the fiber is washed with water until the washing water is substantially free from salt ions, the water is removed from the fiber by further pressing, and the fiber is dried in a stream of air. The fibrous core material having a fiber pH of from 4 to 5 used in accordance with the invention may readily be obtained by this process, particularly when a cupric salt solution adjusted with an acid to a pH-value of from 4 to 5 is used.

The fibrous core material used in accordance with the invention has a more or less pronounced blue coloration, depending on the quantity of copper attached. This blue color, which cannot be washed out under practical conditions, does not affect the use according to the invention in sanitary, hygiene aids and is entirely consistent with psychological perceptions of hygiene.

The bound copper-impregnated fibrous materials are preferably processed on their own, but also may be admixed with other fibers, to form the catamenial tampon core material according to the invention. The core material has the major advantage that bacteria, particularly those encountered in intimate body regions, for example *Escherichia coli, Staphylococcus aureus* and *Candida albicans,* do not proliferate in the core, even under optimal incubation conditions. Even after incubation for 3 days, nutrient cultures charged with the fibrous core materials used in this invention did not emit the unpleasant characteristic odor of corresponding cultures charged with normal wadding.

Since the cation, preferably copper, is firmly attached to the anionic and electronegative groups of the fibers, there is little danger of the cation salt being dissolved by bodily secretions to reach the skin or mucosa in relatively high concentrations and producing toxic side effects.

The outer layer of the catamenial tampon according to this invention may be a fibrous cellulosic material of any type, such as cellulose wadding or viscose wadding. Naturally, the outer layer should not be irritating or in any other way incompatible with contacting the vaginal mucosa.

In one embodiment of this invention, a neutral or untreated fibrous material may be used.

In another, preferred, embodiment of this invention, the outer layer may be a pH-regulating material. Fibrous cellulosic materials of this type are cellulose fibers modified by carboxymethyl groups of the type described above as starting materials for the production of the microbistatic core materials except that instead of a cation-addition, they are converted into their free acid form by treatment with an acid. pH-regulating cellulose fibers such as these have a fiber pH, as measured by DIN 54,275, of below 6, preferably of 3–4. The material for this pH-regulating outer layer has already been described in U.S. patent application Ser. No. 06/660,338 and corresponding German patent application No. P 33 37 443, as well as in U.S. patent application Ser. No. 06/660,334 and corresponding German patent application No. P 33 37 444, all of which are incorporated herein by reference.

In a further embodiment of this invention, the outer layer may be a buffer-impregnated material. The buffer-impregnated material may be obtained by treating cellulosic (preferably viscose) fibers with a physiologically compatible solution comprising citric acid, sodium hydroxide, and other ingredients. The finished material should have an optimum buffering capacity in the pH range of about 4–6. The material for this buffering outer layer has already been described in U.S. patent application Ser. No. 06/615,856 and corresponding published German Patent application No. P 33 20 218, both of which are incorporated herein by reference.

While the primary thrust of this invention is to provide improved catamenial tampons, it should be noted that surgical tampons may also be produced from the same material. Additionally, catamenial pads, panty liners, and the like, may be produced from the above disclosed material, in which instance the "outer layer" is that which is placed closest to the body, and the "core" or "inner layer" may be a flexible panel which is prevented from direct contact with the body by the "outer layer". For such devices, the core layer (i.e. the microbistatic layer) may be sandwiched between two layers of the same material (i.e. the outer layer) or may have a nonporous layer on that side furthest from the body surface.

The catamenial tampons according to the invention may be produced by the following methods:

A strip of web-form fibrous cellulose wadding, such as viscose wadding of pH-regulating carboxymethylated viscose wadding, and a strip of a webform, microbistatically finished fibrous nonwoven are fitted together in such a way that an overlap zone of 2 to 4 cm sufficient for producing a firm joint is formed. The length of the strips is gauged in such a way, taking their thickness into account, that the strip of microbistatically finished fibrous nonwoven can form the core of the tampon while the strip of untreated fibrous cellulose material can form the outer covering of the tampon. As used herein, the term "untreated" also encompasses pH-regulating and buffered materials. The width of the two strips is gauged in such a way that an elongate catamenial tampon of the required size can be produced by any known winding technique, followed by compression. The strip of untreated cellulose material may have a length of 6 to 10 cm and the strip of microbistatically finished fibrous nonwoven a length of 15 to 25 cm. The strip of cellulose material for the outer covering may have a width of 4 to 6 cm and the strip of the microbistatically finished fibrous nonwoven a width of 3.5 to 6 cm. The weight per unit area of the wadding and nonwoven may amount to between 100 and 380 g/m² depending on the required thickness of the tampon. The length and width measurements are based on tampons of average size and may of course be adapted to the desired size of the tampon. However, the strip of microbistatically finished fibrous nonwoven which forms the core of the tampon would not be wider than the strip of untreated wadding and is preferably 10 to 15% narrower than that strip.

In the overlap zone, the two strips are joined firmly together by standard techniques, such as needle punching, calendering or by means of compressed air. Beginning with the microbistatic nonwoven, the strip thus prepared is then wound into a tampon in such a way that the strip of untreated wadding forms the outer covering of the tampon.

Another particularly simple and continuous variant of the process produces catamenial tampons of an outer covering of fibrous cellulose material and a core of partly microbistatic fibrous material. In this variant, the core consists of concentric layers of microbistatic and untreated fibrous material and it is carried out as follows:

Strips of a microbistatically finished fibrous nonwoven are placed centrally on a web of strip-form fibrous cellulose material which is then cut into strips of equal size in such a way that the strips of fibrous cellulose project beyond the strips of nonwoven by 0.5 to 2 cm on one narrow side. The length and width of the strips is gauged in such a way, taking their thickness into account, that an elongate catamenial tampon of the required size can be produced in known manner by winding, followed by compression.

The strips of (unfinished) fibrous cellulose may have a length of 20 to 30 cm and a width of 4 to 6 cm. The strips of microbistatically finished nonwoven lying thereon may have a length of 19 to 29 cm and a width of 3.5 to 6 cm. These measurements are based on fibrous cellulose and nonwoven having a weight per unit area of from 120 to 380 g/m². However, the strips of the microbistatic nonwoven should not be wider than the strip of untreated fibrous cellulose and, preferably, are narrower by 10 to 15% than that strip. Beginning at that end where the strip of fibrous cellulose does not overlap them, the layers of nonwoven lying on top of one another are wound in such a way that the projecting strip of untreated fibrous cellulose forms the outer covering of the tampon. After winding, the tampon is compressed in the usual way.

The tampons according to the invention are preferably provided with a recovery cord. Before the beginning of winding, this recovery cord is tied around that end of the microbistatic strip which is to form the core and the end of the strip folded over the recovery cord.

BRIEF DESCRIPTION OF THE DRAWINGS

FIG. 4 is a schematic diagram of the tampon manufacturing process.

FIG. 5 is a plan view of a microbistatic wadding attached to a longer outer wadding, before folding or winding.

FIG. 6 is the device of FIG. 5 after folding.

FIG. 7 is the device of FIG. 5 after winding.

FIG. 8 is the finished product.

DETAILED DESCRIPTION OF THE INVENTION

Examples

Example 1

Production of the microbistatically finished fibrous material used for Examples 3 and 4

The material in question was produced from a commercially available carboxymethylated viscose fiber ("Viscosorb" 1 S, a product of Lenzing A.G.) characterized by the following:

Water retention capacity: 180–200 ./. (DIN 53,814)
Degree of substitution: 0.09–0.10
Fiber pH: 7.0–7.5 (DIN 54,275)

1 kg of "Viscosorb" 1 S fibers was treated for 30 minutes at room temperature (20° C.) with 20 l of a solution of 20 g of $CuSO_4 \cdot 5\ H_2O$ in 1000 ml of water of which the pH-value had been adjusted to pH 5 with dilute sulfuric acid. The fibers were then squeezed to a moisture content of 200% and washed with water until the washing water was free from sulfate. They were then squeezed again to a moisture content of around 200% and dried for 4 hours at 105° C. in a recirculating-air drying chamber. The fibrous material obtained had the following data:

Fiber pH: 5.6 (DIN 54,275)
Copper content: 1.45% by weight

Example 2

Production of the (non-microbistatic) pH-regulating fibrous cellulose material used for Example 4

This material was produced from the carboxymethylated viscose fiber "Viscosorb" 1 S specified in Example 1.

1 kg of fibers ("Viscosorb" 1 S) was treated for 30 minutes at room temperature with 20 l of 0.2% hydrochloric acid. The fibers were then squeezed to a moisture content of 200% and washed with fully deionized water until the washing water showed a neutral reaction. The fibers were then squeezed again to a moisture content of around 200% and dried for 4 hours at 105° C. in a recirculating-air drying chamber. Testing of the fiber pH by the extrapolation process (DIN 54,275) produced a pH value of 3.0.

Example 3

Figure 1:
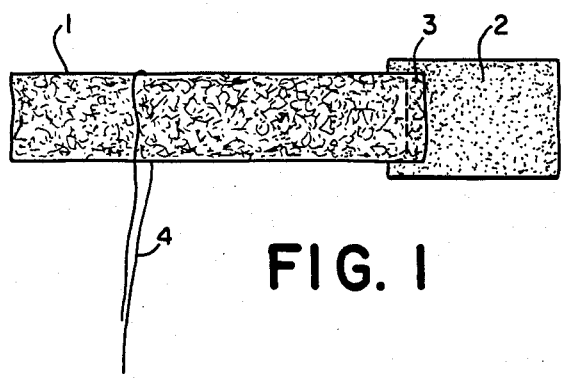
FIG. 1 is a plan view of a microbistatic wadding attached to a shorter outer wadding, before folding or winding.

Production of a catamenial tampon with a core of bacteriostatically finished fibrous material and an untreated outer layer (FIG. 1)

A narrow strip (1) of a fibrous nonwoven 4.5 cm wide and 20 cm long for a weight per unit area of 232 g/m$^2$, which had been microstatically finished in accordance with Example 1, was placed centrally on a 5 cm wide, 8 cm long strip (2) of neutral viscose fiber wadding with a weight per unit area of 165 g/m$^2$, overlapping it at one end by 2.5 cm. The two strips were joined by needle punching in the overlap zone (3). A recovery cord (4) was then tied or looped around the microbistatically finished strip and, after the microbistatically finished strip had been partly folded (5) over the cord, a roll was formed in such a way that the strip of untreated fibrous wadding formed the outer covering. The roll thus formed (6) was then compressed to form the actual tampon by the method normally used for wound tampons.

A wound tampon was obtained of which the outer covering consisted entirely of untreated viscose wadding. By contrast, the core consisted entirely of microbistatically finished fibrous material.

Example 4

Production of a catamenial tampon having a core of concentric layers of microbistatically finished and untreated fibrous material and a pH-regulating covering (FIGS. 5-8).

4 cm wide, 23 cm long strips of a fibrous nonwoven (1) (weight per unit area 190 g/m$^2$) microstatically finished in accordance with Example 1 were placed centrally at intervals of 1 cm on a 5 cm wide web of pH-regulating fibrous cellulose wadding (2) according to Example 2 (weight per unit area 165 g/m$^2$). The fibrous cellulose web was then cut into 24 cm long strips in such a way that it projected 1 cm beyond the strips of microbistatic nonwoven at one end. After the recovery cord (4) had been tied on and the layers of nonwoven partly folded over the cord at that end where there was no overlap, the layer of microbistatic nonwoven passing to the inside (15), a loose wound roll (16) was formed, beginning at the wrapped end, in such a way that the projecting strip of pH-regulating wadding formed the outer covering. The roll thus formed was then compressed to form the actual tampon (17) by the method normally used for wound tampons.

A wound tampon was obtained of which the outer covering consisted entirely of pH-regulating wadding. By constrast, the core consisted of alternating coiled layers of microbistatically finished and pH-regulating fibrous materials.

In Example 3, the untreated layer can be substituted by a pH-regulating or buffered layer. In Example 4, the pH-regulating layer can be substituted by an untreated or buffered layer.

Figure 2:
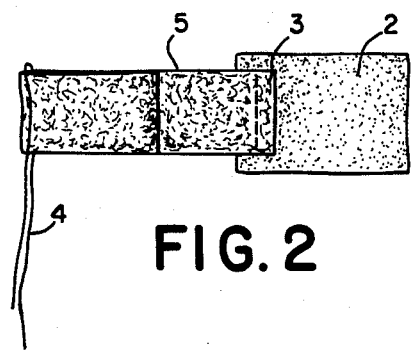
FIG. 2 is the device of FIG. 1 after folding the microbistatic wadding.
Figure 3:
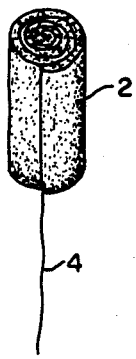
FIG. 3 is the device of FIG. 1 after it is wound.

FIG. 4 is a schematic showing a typical production method for the catamenial tampons of this invention. A strip of microbistatically finished wadding (1) is wound off a reel and fed between a conveyor belt (9) and guide belt (10) to a cutting station (11) where the strip is cut into desired lengths. A strip of neutral, pH-regulating, or buffered viscose wadding (2) is then introduced from a second reel located below. The strip (2) may act as a support bed for the strip (1). The cut lengths of strip (1) and strip (2) are then further transported by a further conveyor belt (9) and guide belt (10) to a second cutting station (11) where the strip (2) is also cut into desired lengths. The cut of strip (2) must, of course, be between the ends of previously cut strip (1Y) lengths, so that these lengths are not cut again. The strips (1 and 2) of wadding lying on top of each other (12) are then further transported by a conveyor belt (9) to a winding and pressing device (13) where the recovery cord (4) is looped and the two cut lengths (1 and 2) are sewn and folded as shown in FIGS. 1 and 2 or simply folded as shown in FIGS. 5 and 6, after which they are wound (16) as shown in FIGS. 3 and 7 and compressed into a catamenial tampon (17) as shown in FIG. 8.

Where a catamenial pad, panty liner, or like device, is to be manufactured, the strips (1 and 2) are of a suitable width and the cutting stations (11) may be dies capable of cutting the product to a desired shape. Obviously, cut lengths of strips (1 and 2) would then be transported not to a winding and pressing device (13) but rather to a bonding or laminating device (not shown). A further, preferably nonporous layer, preferably a plastic film, may be bonded to the other side of the microbistatic layer, so as to contain all fluids within the device. This can be accomplished by adding another roll carrying such material and another cutting station, or by various other well known means, none of which are shown.

I claim:

1. A catamenial device having at least two adjacent layers of material wherein said layers are at least:
   (A) An outer layer for placement next to the skin or mucous surfaces consisting essentially of non-microbistatic, treated or untreated, porous, fibrous, cellulosic material; and
   (B) an inner layer or core consisting essentially of at least partially an absorbent fibrous microbistatic material containing a microbistatic agent which is chemically bound to said fibrous material by attaching an anion to a cellulose anhydroglucose unit and capping said anion with a microbistatically effective cation so that said agent cannot leach through said outer layer, present in a microbistically effective amount.

2. A catamenial device having at least two adjacent layers of material wherein said layers are at least:
   (A) an outer layer for placement next to the skin or mucous surfaces consisting essentially of non-microbistatic, treated or untreated, porous, fibrous, cellulosic material; and
   (B) an inner layer or core consisting essentially of at least partially an absorbent fibrous microbistatic material containing a microbistatic agent which is chemically bound to said fibrous material so that said agent cannot leach through said outer layer, present in a microbistatically effective amount; and wherein said microbistatic material consists essentially of cellulose fibers modified by anionic moieties of at least one of the general formulae: $-PO_3H^{(-)}$; $-(CH_2)_n-PO_3H^{(-)}$; $-(CH_2)_n-SO_3^{(-)}$; or $-(CH_2)_n-COO^{(-)}$; wherein n is from 1 to 3; which anionic moieties are each attached through an oxygen atom to a cellulose anhydroglucose unit; wherein sufficient of said anionic moieties are present, and sufficient of said present anionic moieties are capped by a cation, to form a microbistatic-effective material, said cation being copper, silver, zinc, cadmium, chromium, nickel, cetyltrimethylammonium, lauryldimethylbenzylammonium, or any mixture thereof.

3. The device of claim 2 wherein said cellulose fibers bind from about 0.1 to about 3% by weight of said cations, based on the weight of said fibers.

4. The device of claim 2 wherein said cation is cupric, and said cellulose fibers bind from about 0.1 to about 2% by weight of copper, based on the weight of said fibers.

5. The device of claim 4 wherein said cellulose fibers bind from about 0.2 to about 0.8% by weight of said copper, based on the weight of said fibers.

6. The device of claim 2 wherein said at least one anionic moiety has an average 0.01 to 0.3 said moieties per said anhydroglucose unit.

7. The device of claim 6 wherein said anionic moiety is carboxymethyl.

8. The device of claim 1 wherein said microbistatic material consists essentially of cellulose fibers having carboxymethyl anions attached through oxygen atoms to cellulose anhydroglucose units, said carboxymethyl anions being present in an average 0.01 to 0.3 said anions per anhydroglucose unit, and wherein sufficient of said anionic moieties are capped by cupric cations to form a microbistatically effective material having from about 0.1 to about 2% by weight of copper, based on the weight of said fibers.

9. The device of claim 1 wherein said outer layer consists essentially of untreated material.

10. The device of claim 2 wherein said outer layer consists essentially of untreated material.

11. The device of claim 4 wherein said outer layer consists essentially of untreated material.

12. The device of claim 8 wherein said outer layer consists essentially of untreated material.

13. The device of claim 1 wherein said outer layer consists essentially of pH-regulating cellulose material in which carboxymethyl moieties are attached through oxygen atoms to cellulose anhydroglucose units, said carboxymethyl moieties being present in on average 0.01 to 0.3 said anions per anhydroglucose unit, and substantially all of said carboxymethyl moieties being in their free acid form.

14. The device of claim 2 wherein said outer layer consists essentially of pH-regulating cellulose material in which carboxymethyl moieties are attached through oxygen atoms to cellulose anhydroglucose units, said carboxymethyl moieties being present in on average 0.01 to 0.3 said anions per anhydroglucose unit, and substantially all of said carboxymethyl moieties being in their free acid form.

15. The device of claim 4 wherein said outer layer consists essentially of pH-regulating cellulose material in which carboxymethyl moieties are attached through oxygen atoms to cellulose anhydroglucose units, said carboxymethyl moieties being present in on average 0.01 to 0.3 said anions per anhydroglucose unit, and substantially all of said carboxymethyl moieties being in their free acid form.

16. The device of claim 8 wherein said outer layer consists essentially of pH-regulating cellulose material in which carboxymethyl moieties are attached through oxygen atoms to cellulose anhydroglucose units, said carboxymethyl moieties being present in on average 0.01 to 0.3 said anions per anhydroglucose unit, and substantially all of said carboxymethyl moieties being in their free acid form.

17. The device of claim 1 wherein said outer layer consists essentially of buffer impregnated fibers carrying the residue of a buffer solution comprising citric acid and sodium hydroxide, said layer having an optimum capacity in the pH-range of about 4-6.

18. The device of claim 2 wherein said outer layer consists essentially of buffer impregnated fibers carrying the residue of a buffer solution comprising citric acid and sodium hydroxide, said layer having an optimum capacity in the pH-range of about 4-6.

19. The device of claim 4 wherein said outer layer consists essentially of buffer impregnated fibers carrying the residue of a buffer solution comprising citric acid and sodium hydroxide, said layer having an optimum capacity in the pH-range of about 4-6.

20. The device of claim 8 wherein said outer layer consists essentially of buffer impregnated fibers carrying the residue of a buffer solution comprising citric acid and sodium hydroxide, said layer having an optimum capacity in the pH-range of about 4-6.

21. The device of claim 1 in the form of a generally cylindrical tampon in which said inner layer comprises the core material and in which the outer surface is completely enclosed by said outer layer.

22. The device of claim 12 in the form of a generally cylindrical tampon in which said inner layer comprises the core material and in which the outer surface is completely enclosed by said outer layer.

23. The device of claim 16 in the form of a generally cylindrical tampon in which said inner layer comprises the core material and in which the outer surface is completely enclosed by said outer layer.

24. The device of claim 20 in the form of a generally cylindrical tampon in which said inner layer comprises the core material and in which the outer surface is completely enclosed by said outer layer.

25. The device of claim 1 in the form of a generally cylindrical tampon in which the inner portion comprises alternating spiralling concentric layers of said inner layer material and said outer layer material and the outer surface is completely enclosed by said outer layer material.

26. The device of claim 12 in the form of a generally cylindrical tampon in which the inner portion comprises alternating coiled concentric layers of said inner layer material and said outer layer material, and wherein the outer surface is completely enclosed by said outer layer material.

27. The device of claim 16 in the form of a generally cylindrical tampon in which the inner portion comprises alternating coiled concentric layers of said inner layer material and said outer layer material, and wherein the outer surface is completely enclosed by said outer layer material.

28. The device of claim 20 in the form of a generally cylindrical tampon in which the inner portion comprises alternating coiled concentric layers of said inner layer material and said outer layer material, and wherein the outer surface is completely enclosed by said outer layer material.

29. The device of claim 1 in the form of a catamenial pad or panty liner wherein a nonporous third layer is on the uncovered side of said inner layer.

30. The device of claim 12 in the form of a catamenial pad or panty liner wherein a nonporous third layer is on the uncovered side of said inner layer.

31. The device of claim 16 in the form of a catamenial pad or panty liner wherein a nonporous third layer is on the uncovered side of said inner layer.

32. The device of claim 20 in the form of a catamenial pad or panty liner wherein a nonporous third layer is on the uncovered side of said inner layer.

* * * * *